US010317358B1

(12) United States Patent
Sagues et al.

(10) Patent No.: US 10,317,358 B1
(45) Date of Patent: Jun. 11, 2019

(54) SYSTEMS AND METHODS FOR CONTACTLESS ASSESSMENT OF STRUCTURES BURIED IN SOIL

(71) Applicants: Alberto A. Sagues, Lutz, FL (US); William Clarence Ruth, St. Petersburg, FL (US); Leonidas Philip Emmenegger, Tarpon Springs, FL (US); Enrique Alberto Paz Velasquez, Tampa, FL (US)

(72) Inventors: Alberto A. Sagues, Lutz, FL (US); William Clarence Ruth, St. Petersburg, FL (US); Leonidas Philip Emmenegger, Tarpon Springs, FL (US); Enrique Alberto Paz Velasquez, Tampa, FL (US)

(73) Assignee: University of South Florida, Tampa, FL (US)

( * ) Notice: Subject to any disclaimer, the term of this patent is extended or adjusted under 35 U.S.C. 154(b) by 87 days.

(21) Appl. No.: 15/460,156

(22) Filed: Mar. 15, 2017

Related U.S. Application Data

(60) Provisional application No. 62/308,548, filed on Mar. 15, 2016.

(51) Int. Cl.
  *G01N 27/24* (2006.01)
  *G01N 17/04* (2006.01)
  *G01N 17/00* (2006.01)

(52) U.S. Cl.
  CPC ........... *G01N 27/24* (2013.01); *G01N 17/006* (2013.01); *G01N 17/04* (2013.01)

(58) Field of Classification Search
  CPC ....... G01N 27/24; G01N 17/006; G01N 17/04
  See application file for complete search history.

(56) References Cited

U.S. PATENT DOCUMENTS

| | | |
|---|---|---|
| 3,626,341 A | 12/1971 | Dao |
| 4,649,336 A | 3/1987 | Bindner et al. |
| 4,806,850 A * | 2/1989 | Saumade ............... G01N 17/02 204/404 |
| 4,861,453 A | 8/1989 | Matsuoka et al. |
| 4,942,354 A | 7/1990 | Miller |
| 5,136,247 A | 8/1992 | Hansen |
| 5,498,974 A | 3/1996 | Verkuil |

(Continued)

OTHER PUBLICATIONS

Huang, et al., "Monitoring Soil Contaminations Using a Contactless Conductivity Probe", Geophysical Prospecting, 1995, 43, 759-778.

(Continued)

*Primary Examiner* — Charlie Y Peng
(74) *Attorney, Agent, or Firm* — Thomas | Horstemeyer, LLP

(57) ABSTRACT

In one embodiment, reinforced soil is assessed using a non-contact method including positioning a reference electrode in close proximity to a surface of the soil without contacting the electrode to the soil surface, vibrating the electrode with a vibration generator, and measuring an electrical potential difference between the electrode and the soil surface, the potential difference being indicative of the condition of a portion of a reinforcement member positioned below the soil surface at the location of the electrode.

18 Claims, 7 Drawing Sheets

(56) References Cited

U.S. PATENT DOCUMENTS

| | | | | |
|---|---|---|---|---|
| 5,841,282 A | * | 11/1998 | Christy | A01B 79/005 |
| | | | | 324/347 |
| 5,945,594 A | | 8/1999 | Kendig et al. | |
| 6,856,159 B1 | | 2/2005 | Tolk | |
| 2002/0175892 A1 | * | 11/2002 | Braun | G06F 3/016 |
| | | | | 345/156 |
| 2003/0169058 A1 | * | 9/2003 | Pierre | G01N 17/02 |
| | | | | 324/700 |
| 2003/0175945 A1 | * | 9/2003 | Thompson | B82Y 35/00 |
| | | | | 435/287.2 |
| 2006/0122478 A1 | | 6/2006 | Sliepen | |
| 2010/0039127 A1 | * | 2/2010 | Orazem | C23F 13/04 |
| | | | | 324/718 |
| 2013/0300419 A1 | * | 11/2013 | Hibbs | G01V 3/088 |
| | | | | 324/348 |
| 2015/0185133 A1 | * | 7/2015 | Murray | G01N 17/02 |
| | | | | 205/775.5 |
| 2017/0202202 A1 | * | 7/2017 | Crisp | A01M 19/00 |

OTHER PUBLICATIONS

Noras, "Non-Contact Surface Charge/Voltage Measurements" Capacitive probe-principle of operation. No. 3001, 2002, Trek, Inc.

Electric-Field Contact-Less Sensing System, Reference manual, MC33794.

Student Poster Session poster "Application of a Macroscopic Kelvin Probe for Potential Survey of Reinforcement in Soil and Cementitious Filler" presented by W. Ruth during the NACE International Annual Meeting, Corrosion 2015, Dallas, Texas, Mar. 15-18, 2015.

Student poster "Application of a Macroscopic Kelvin Probe for Potential Survey of Reinforcement in Soil and Cementitious Filler" presented by W. Ruth at the American Institute of Chemical Engineers Southern Student Regional Conference, Clearwater Beach, FL, Apr. 10-12, 2015.

Journal paper "Kelvin Probe electrode for contactless potential measurement on concrete—Properties and corrosion profiling application", A. Sagüés and M. Walsh, Corrosion Science, vol. 56, pp. 26-35 (2012).

Conference paper "Novel Kelvin Probe electrode for non-intrusive corrosion rate evaluation of steel in aged concrete structures", M.T. Walsh and A.A. Sagüés, pp. 569-575 in Proceedings of the 1st International Conference on Ageing of Materials & Structures, K. van Breugel and E.A.B. Koenders, Eds., Delft University of Technology, Delft, The Netherlands, 2014.

Conference paper "Contactless Kelvin Probe Electrode for Potential and Polarization Resistance Measurements of Reinforcing Steel in Concrete", Alberto A. Sagüés and Michael T. Walsh, Paper No. A362, 9 pp., Corrosion 2014, NACE International, Houston, 2014.

Conference Poster Contactless Electrode for Fast Survey of Concrete Reinforcement Corrosion by A. Sagüés and L. Emmenegger, Transportation Research Board 94th annual meeting, Jan. 11-15, 2015, Washington, DC.—Session: 296.

Akid et al., "Scanning vibrating reference electrode technique: a calibration study to evaluate the optimum operating parameters for maximum signal detection of point source activity", Electrochimica Acta, 49, 2004, 2871-2879.

Hu et al., "Recent progress in corrosion protection of magnesium alloys by organic coatings", Progress in Organic Coatings 73 (2012), 129-141.

Jamil et al., "Electrochemical behaviour of amino alcohol-based inhibitors used to control corrosion of reinforcing steel", Electrochimica Acta 49, 2004, 2753-2760.

Liu et al., "A MEMS-based piezoelectric power generator array for vibration energy harvesting", Microelectronic Journa 39(2008), 802-806.

Yee et al., "Application of a Kelvin Microprobe to the Corrosion of Metals in Humid Atmospheres", J. Electrochem. Soc. 138(1) 1991, 55-61.

Zhang et al., Localized corrosion behaviour of reinforcement steel in simulated concrete pore solution, Corrosion Science 51 (2009), 2130-2138.

Non-final Office Action dated Jun. 22, 2016 in U.S. Appl. No. 13/905,761.

Final Office Action dated Jan. 12, 2017 in U.S. Appl. No. 13/905,761.

Non-final Office Action dated May 15, 2017 in U.S. Appl. No. 13/905,761.

Final Office Action dated Oct. 23, 2017 in U.S. Appl. No. 13/905,761.

Non-final Office Action dated Aug. 2, 2018 in U.S. Appl. No. 13/905,761.

\* cited by examiner

SYSTEMS AND METHODS FOR CONTACTLESS ASSESSMENT OF STRUCTURES BURIED IN SOIL

CROSS-REFERENCE TO RELATED APPLICATION

This application claims priority to U.S. Provisional Application Ser. No. 62/308,548, filed Mar. 15, 2016, which is hereby incorporated by reference herein in its entirety.

NOTICE OF GOVERNMENT-SPONSORED RESEARCH

This invention was made with Government support under NCHRP-IDEA Project 176 awarded by the National Cooperative Highway Research Program. The Government has certain rights in the invention.

BACKGROUND

Building foundations, highway tunnels, pipelines, and many other areas of the nation's infrastructure rely on adequate corrosion performance of buried metal. A representative example is provided by mechanically stabilized earth walls (MSEW), which are critical structural components in nearly all highways. The walls are often reinforced with galvanized steel buried in the soil. Voids sometimes occur in the soil and are typically filled with cement-based, hardened, controlled low-strength material (CLSM). In such cases, soil/CLSM electrochemical macrocells may develop and aggravate reinforcement corrosion.

Half-cell potential surveys of the soil, CLSM, and similar surfaces can be used for non-destructive corrosion monitoring by identifying macroscopic anodic and cathodic regions. Potential measurements can also serve to diagnose and adjust cathodic protection systems if they are needed for corrosion control. Such potential measurements commonly use conventional copper-copper(II) sulfate electrodes (CSEs), which require physical contact with the surface (and its disturbance) as well as waiting times to have a stable reading, which are both disadvantages in extensive surveys. It would, therefore, be desirable to have alternative systems and methods for monitoring buried reinforcement structures that do not have these drawbacks.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
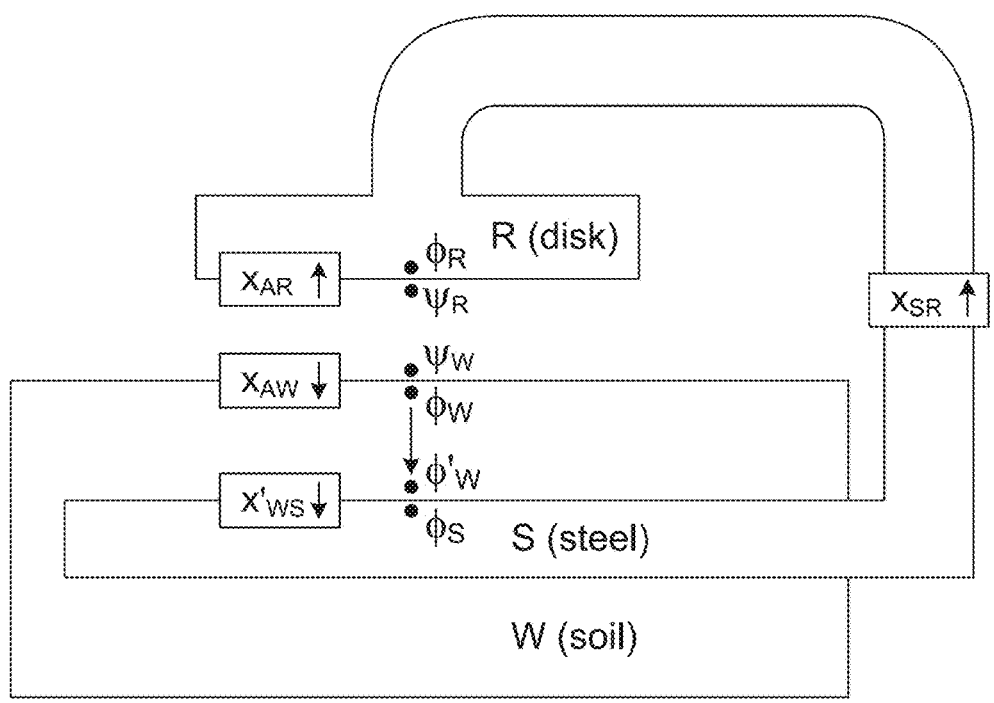
FIG. 1 is a schematic diagram that illustrates potentials and interfacial potential differences in a Kelvin probe arrangement for steel or any other buried metal in soil.

As described above, it would be desirable to have alternative systems and methods for monitoring the corrosion of reinforcement or other metallic structures buried in soil. Disclosed herein are embodiments of such systems and methods. In some embodiments, the disclosed systems utilize Kelvin probes to measure soil surface electrical potentials so that a contactless measurement procedure can be performed that does not depend upon a shared electrolyte and that is inherently non-disruptive to the region sampled by the probe.

In the following disclosure, various specific embodiments are described. It is to be understood that those embodiments are example implementations of the disclosed inventions and that alternative embodiments are possible. All such embodiments are intended to fall within the scope of this disclosure.

A fast, contactless corrosion assessment system based on the Kelvin probe principle is disclosed herein. The concept, applied here for the first time for soil and CLSM measurements, is also explored for possible monitoring of cathodic protection in soils. As described below, the probe does not require contact with the soil surface and provides nearly instantaneous readings. With such a system, applications for fast monitoring of large installations or over long distances from moving vehicles for monitoring of pipelines or other extended systems can be a reality.

A Kelvin probe is essentially a parallel-plate capacitor having one vibrating side that is used to determine the natural potential difference between a sensing electrode shaped like a disk or comparable configuration (hereafter referred to for brevity as a disk) and a sample surface. By recording the potential required to null the current generated by the Kelvin probe's sensing disk, a map of surface potentials can be obtained.

Kelvin probes determine the potential difference E between two surfaces designated as the working surface and the reference surface, respectively. In the case of reinforced soil, the working surface is a small (top) portion of the outer soil surface and the reference surface is the surface on one side of a macroscopically small (e.g., approximately 10-centimeter (cm) diameter) electrode (e.g., disk) made of a suitable metallic material, for example, gold or stainless steel with a stable passive film, or even galvanized steel if its surface condition is stable enough. The disk and the soil surface are spaced a small (relative to the disk dimensions) distance, h, apart so as to approximate a parallel-plate capacitor configuration. The disk is electrically connected through electrical conductors (e.g., wires) to the metallic reinforcement structure, such as galvanized steel bars (referred to in the following for brevity as steel), buried in the soil or soil filler material. The steel bar surface is electrically connected to the external surface of the soil by an electrolytic path provided mainly by the water in the soil. Consequently, the soil and the reference (disk) surfaces are joined through an electronic and electrolytic conductive path with associated interfaces that determine the value of E. The relationship linking electrical charge Q and potential difference E across a capacitor with capacitance C is $$Q = E \cdot C \qquad \text{Equation 1}$$

For plates spaced by a small gap, the capacitance can be approximated by $$C = \varepsilon \cdot \varepsilon_0 \cdot A/h \qquad \text{Equation 2}$$

where $\varepsilon$ is the dielectric constant of the medium in the gap between the plates (normally air, $\varepsilon \sim 1$), $\varepsilon_0$ is the permittivity of vacuum, and A is the one-sided surface area of the smaller of the plates, in this case the reference surface. Because E is fixed by the characteristics of the intervening conducting and interfacial chain, if h is changed from one static position to another, the value of Q changes as well to satisfy Equations 1 and 2. In the Kelvin probe, h is cyclically varied with time by attaching the reference disk to the end of an electrically-insulating, longitudinally-vibrating stem. Consequently, Q changes cyclically as well, resulting in an alternating current $I_A$ circulating through the conductive path. If a potential source with a known potential E' selected at will is inserted in that path (e.g., into a break made in the connecting wire to the rebar), the potential between the reference and soil surface becomes E+E'. When E'=−E, the potential across the capacitor is zero and the alternating current vanishes. This then permits determining the value of E by varying E' until $I_A$=0, a condition that can be reached with great sensitivity by adequate electronic amplification. The zeroing process can be made manually or performed automatically and promptly with ordinary control circuitry, yielding an immediate record of the value of E.

With interfaces having well-defined boundaries and locally-uniform electric charge profiles, the potential E measured by the Kelvin probe is the difference between the Volta (outer) potential $\Psi_R$ of the reference surface and the Volta potential of $\Psi_W$ of the working surface being examined $$E = \Psi_R - \Psi_W \qquad \text{Equation 3}$$

The metallic reference disk generally approximates those conditions and may be considered to have a well-defined, spatially averaged $\Psi_R$ value. The soil or soil void filler surface is quite heterogeneous, as is the distribution of the electrolyte responsible for much of the electric charge configuration in the material. Hence, $\Psi_W$ can be considered only as an effective value, i.e., that of an ideal conductor that would yield the same experimental results as those obtained with the soil. Thus, $\Psi_W$ may be viewed as representing an approximate average of the potential of the surface of the soil beneath the footprint of the reference surface disk. Lateral heterogeneity up to the centimeter scale (pore space-soil or soil void filler particles domain) is expected to be reasonably averaged beneath the disk, but some sensitivity to the distribution of the soil components which can be greater than several centimeters, can be anticipated.

The value of E measured by the Kelvin probe can be determined by the system schematically illustrated in FIG. 1. For simplicity, only two different metals are assumed to be involved, one for the reference surface R and one for the steel bar S. The respective inner (Galvani) potentials are designated $\Phi_R$ and $\Phi_S$ with a corresponding interfacial potential difference $X_{SR} = \Phi_R - \Phi_S$. The arrows in the figure indicate that the stated difference of potential is added to the potential at the tail to obtain that at the head. Designations for the medium-air interfacial potential differences are respectively $X_{AR} = \Phi_R - \Psi_R$ and $X_{AW} = \Phi_W - \Psi_W$, and for the metal-electrolyte interfacial potential $X'_{WS} = \Phi_S - \Psi_W$. Both $\Phi_W$ and $\Phi'_W$ are effective magnitudes representing a similar idealization as that noted above for $\Psi_W$. The values of $\Phi_W$ and $\Phi'_W$ are, in general, not the same because of the ohmic potential drop created by the corrosion macrocell currents in the soil and of electrolyte composition gradients within the soil that cause macroscopic junction potentials and electro-kinetic effects. The resulting difference is designated as $\Delta\Phi_W = \Phi'_W - \Phi_W$. Ohmic drops and similar effects within the metals themselves are treated as negligible in the present analysis. Applying the above definitions to Equation 3 yields $$E = X'_{WS} + X_{SR} - X_{AR} + X_{AW} + \Delta\Phi_W \qquad \text{Equation 4}$$

Figure 2:
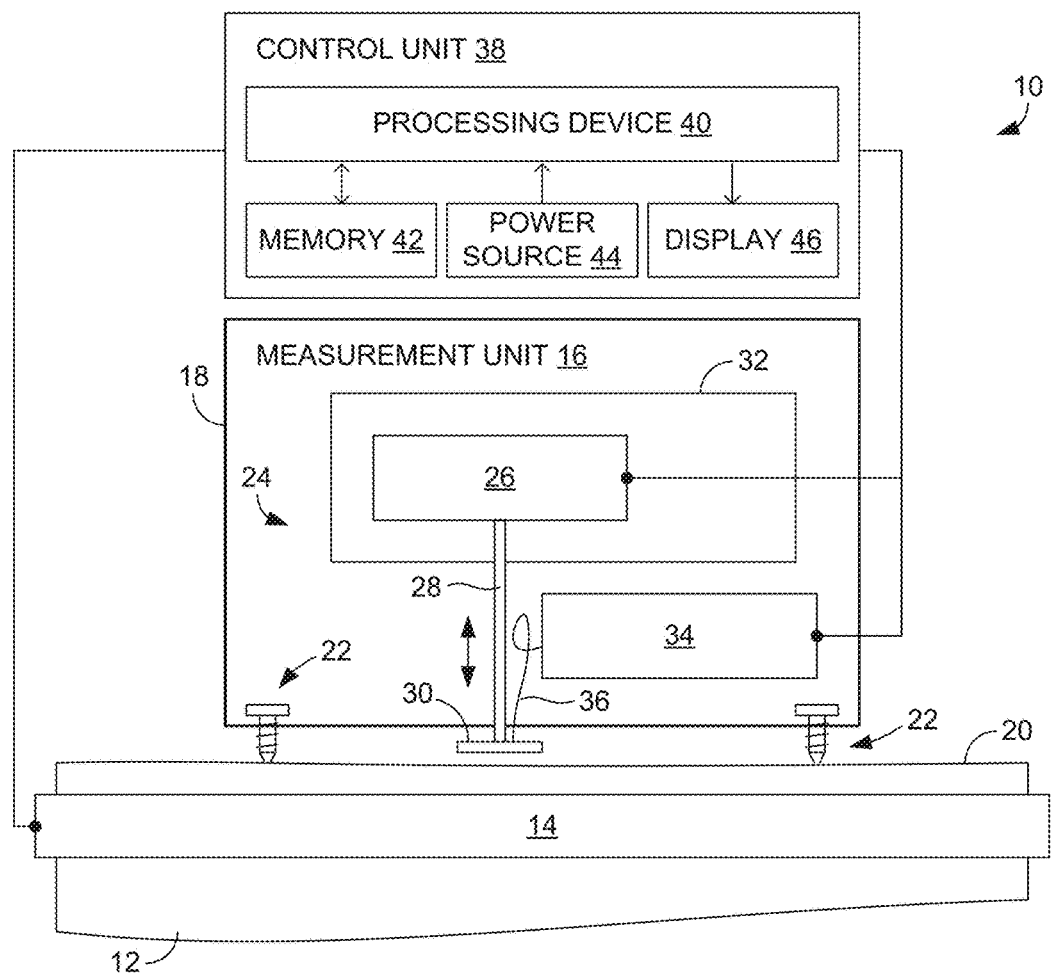
FIG. 2 is a schematic view of an embodiment of a non-contact reinforced soil assessment system that utilizes a Kelvin probe.

FIG. 2 illustrates an example non-contact reinforced soil assessment system 10 incorporating a Kelvin probe that can be used to identify possible corrosion of steel reinforcement buried within soil. The steel reinforcement is represented by a steel reinforcement member 14 that is shown buried within the soil 12. As shown in FIG. 2, the system 10 comprises a measurement unit 16 that includes an outer housing 18 made of a conductive material, such as steel. The measurement unit 16 is supported above an outer (top) surface 20 of the soil 12 with adjustable feet 22. When provided, the adjustable feet 22 can be used to adjust the height of the measurement unit 16 relative to the soil surface 20 as well as the gap between a reference electrode of the system 10 and the surface. Notably, the feet 22 can be replaced with wheels to facilitate movement of the system along the soil surface 20 (see FIGS. 3 and 4).

Supported by the outer housing 18 is a Kelvin probe 24 that comprises a vibration generator 26, a stem 28 that extends from the vibration generator, and a dry reference electrode 30 that is mounted to a distal tip of the stem. In some embodiments, the vibrating generator 26 comprises an electromagnetic voice coil that linearly displaces the stem 28, and therefore the reference electrode (see double-headed arrow), in response to a magnetic field generated from current passing through the coil. As is also shown in FIG. 2, the vibration generator 26 is electromagnetically shielded by a grounded inner shield 32, which can be made of steel or another electrically-conductive material.

The reference electrode 30 can comprise a metal disk or alternatively shaped element having a diameter or equivalent dimension ranging from several millimeters to several centimeters. Irrespective of its shape or size, the electrode 30 has a planar outer surface that faces the soil surface 20. Example metals include pure, corrosion-resistant metals, such as gold, and metal alloys, such as stainless steel, that may require a passive film for corrosion resistance, or other electrically conducting materials if stable enough surface conditions exist. The stem 28 can comprise a shaft of an insulating material that is not prone to static charge buildup, such as a polymeric material or wood. Provided within the housing 18 along with the vibration generator 26 is a preamplifier 34 that is electrically coupled to the reference electrode 30, for example with a conductive wire 36.

The reinforced soil assessment system 10 further comprises a control unit 38 that controls operation of the system. While the control unit 38 can be separate from the measurement unit 16 as shown in FIG. 2, it is noted that, in some embodiments, the control unit and the measurement unit can be integrated into a single device. In the example of FIG. 2, the control unit 38 includes a processing device 40, memory 42, a power source 44, and a display 46. The control unit 38 is electrically coupled to the reinforcement member 14, the vibration generator 26, and the preamplifier 34.

As shown in FIG. 2, the measurement unit 16 can be placed on top of the surface 20 of the soil 12 in which the reinforcement member 14 is buried. When the feet 22 of the unit 16 are properly adjusted, the reference electrode 30 will be approximately 1 to 2 cm from the soil surface 20. When the system 10 is activated, for example by selecting an appropriate button on a user interface of the control unit 38 (not shown), the control unit enables current supplied by the power source 44 to flow to the vibration generator 26 so that it will linearly oscillate the reference electrode 30 toward and away from the soil surface 20. In some embodiments, the reference electrode 30 moves within a range of approximately 0.8 to 1.2 mm between its uppermost and lowermost positions at a frequency of approximately 150 Hz.

As the reference electrode 30 oscillates, electrical signals from the electrode are amplified by the preamplifier 34 and captured by the control unit 38, which stores them within memory 42. Optionally, the signals are first processed by the processing device 40 to identify the electrical potential E represented by the signals. The electrical potential can also be displayed to the user with the display 46.

Figure 3:
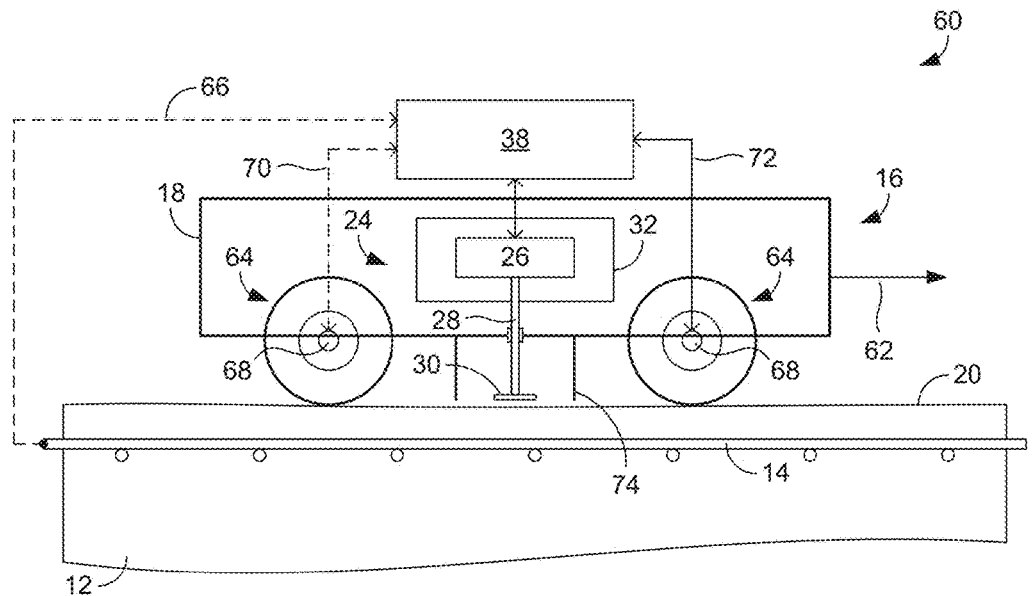
FIG. 3 is a schematic side view of a second embodiment of a non-contact reinforced soil assessment system that utilizes a Kelvin probe.
Figure 4:
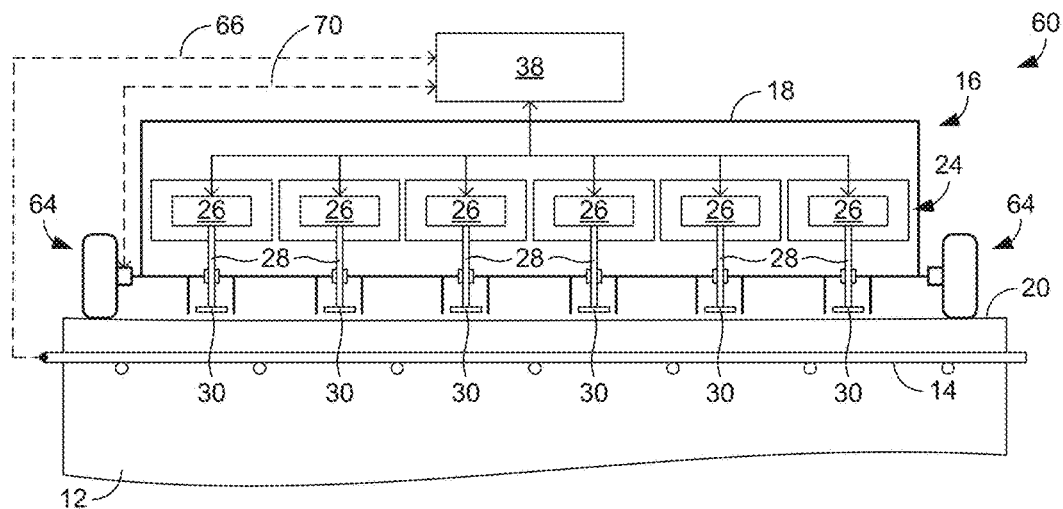
FIG. 4 is a schematic end view of the non-contact reinforced soil assessment system of FIG. 3.

As mentioned above, the non-contact reinforced soil assessment system can comprise wheels instead of feet to enable the system to be moved along the soil surface. FIGS. 3 and 4 illustrate an example of such a system 60. As is apparent from these figures, the system 60 is similar in many ways to the system 10 shown in FIG. 2. Accordingly, with reference to FIG. 3, the system 60 also comprises a measurement unit 16 that includes an outer housing 18 and a Kelvin probe 24 that comprises a vibration generator 26, a stem 28, and a dry reference electrode 30. A preamplifier (not shown) can also be provided within the housing 18. In addition to the measurement unit 16, the system 60 includes a control unit 38 that, for example, can include a processing device, memory, a power source, and a display.

Unlike the system 10, however, the system 60 is adapted to be moved (e.g., pulled) across the soil surface 20 (e.g., by a motorized vehicle) in the direction indicated by the arrow 62. Accordingly, wheels 64 are mounted to the measurement unit 16 to enable it to roll across the soil surface 20. In some embodiments, force distribution members, such as planks of cardboard, wood, or another rigid material can be positioned beneath the wheels to distribute the force applied to the soil surface 20 by the wheels. Alternatively, continuous track assemblies (not shown) can be used to distribute the force. Other controlled-height, hovering, and suspension arrangements, such as very low altitude flight drones, can be used as well.

As is further illustrated in FIG. 3, the control unit 38 can be electrically coupled to the reinforcement member 14 buried in the soil 12 with an electrical conductor 66 in similar manner to that shown in FIG. 2. In such a case, the system 60 operates in an absolute mode in which all measurements are taken relative to the same reference. Alternatively, in cases in which the wheels are electrically conductive (e.g., when the wheels have electrically-conductive elastomeric tires and contact the soil surface 20), the control unit 38 can be electrically coupled to the wheel's axle 68 with a different electrical conductor 70 so that measurements can be taken in a differential or relative mode. In such a mode, the measurements are taken relative to different reference points along the soil surface 20 (i.e., the points on the surface with which the wheel 64 is in contact). In such a case, the nature of the contact with the soil 12 does not matter as it is nulled out by the circuitry. The measurements taken at different points along the surface can then be compared to each other as a means of identifying hot spots that are indicative of active corrosion. Such a mode may be a more attractive alternative from the point of view of operation speed because this mode does not require a trailing wired contact to the rebar assembly and the rolling system is completely self-contained.

Because measurements are taken at multiple points along the length of the soil surface 20, it is important to determine where each measurement was taken. To this end, the control unit 38 can be electrically coupled with another electrical conductor 72 to a distance measurement device (not shown) mounted to the axle 68 of one of the wheels 64. With such a device, the angular position of the wheel 64 at the point at which each measurement is taken can be recorded and, with knowledge of the diameter of the wheel 64, can be converted into a linear distance.

As is further shown in FIG. 3, the measurement unit 16 can also include a grounded shield 74 that shields the electrode 30 from electromagnetic interference. In some embodiments, the shield 74 comprises a cylindrical metal element that extends downward from the outer housing 18 and encircles the stem 28 and the reference electrode 30.

FIG. 4 shows the reinforced soil assessment system 60 in an end view. As is apparent from FIG. 4, the measurement unit 16 can comprise multiple Kelvin probes 24 that are aligned in an array along the width of the unit. In such a case, multiple measurements across the width of the soil surface 20 can be simultaneously recorded. Each Kelvin probe 24 can have the same configuration as that described above in relation to FIG. 3 and each can have its own reference electrode shield 74.

Figure 5:
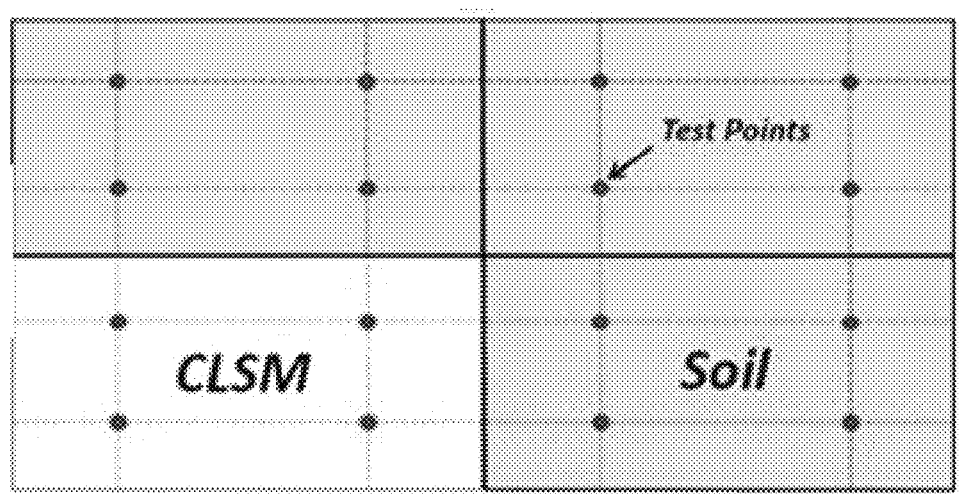
FIG. 5 is a schematic diagram of a soil test box.

Testing was conducted to confirm the viability of the above-described designs on soil. As shown in FIG. 5, a large-scale soil test box was used that simulates an MSEW with a CLSM void repair. For these tests, the working electrode comprised an interconnected pair of buried, galvanized mesh elements, with one element embedded in CLSM and the other embedded in adjacent soil, thereby forming a low-intensity corrosion macrocell. In additional tests, the system was wired as a simulated cathodic protection (CP) system, which created a greater surface potential gradient. In some embodiments, the Kelvin probe comprised an array of two Kelvin probes (i.e., a dual-sensor array).

The Kelvin probe's ability to measure surface potentials of soil and CLSM systems was examined by comparing results to measurements with a conventional CSE. The tests also evaluated the ability of the probe to monitor time-dependent potentials, as may be used for adjustment of a cathodic protection system for soil reinforcement.

The soil and CLSM regions were moderately leveled before testing to prevent accidental contact with the Kelvin probe sensing disk and the soil or the CLSM. The dual-sensor array had electric shields to minimize interfering signals. Conventional potential data for comparison were gathered with a CSE electrode connected to a high-impedance voltmeter and the embedded reinforcement, as is customary.

For the basic probe tests, a temporary, round, stainless steel surface anode was used to simulate a cathodic protection system to evaluate the ability of the probe to detect time-dependent polarization and depolarization effects. For the dual-sensor array tests, the anode was formed as a narrow rectangle near the center of a long edge of the box surface.

Figures 6A, 6B:
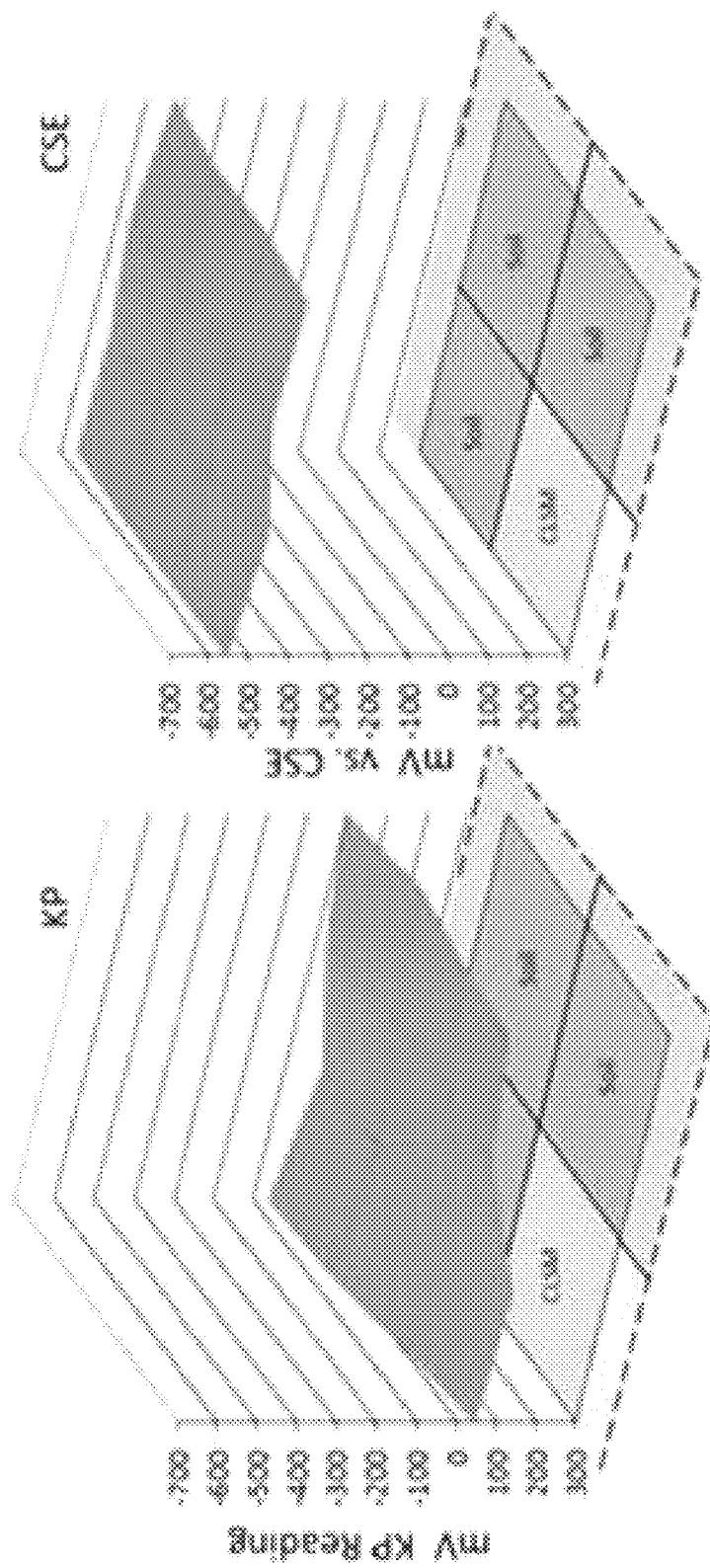
FIGS. 6A and 6B are comparative Kelvin probe (6A) and conventional CSE (6B) potential mapping. The dashed lines identify the full soil testing box.

Through the testing, the Kelvin probe was observed to operate stably and with adequate reproducibility on the both the CLSM and the soil. The potential values that obtained were suitable to create a surface potential map, as shown in FIG. 6A. The probe response on the CLSM and soil was nearly instantaneous, i.e., with a characteristic response time in the order of 1 second. For the tested system, which had relatively weak active corrosion macrocells, the potential gradient was moderately flat (~160 mV range over 2 m). A comparably flat profile (~60 mV range) was observed when conducting the same measurements using a traditional CSE, as shown in FIG. 6B. The values indicated by the Kelvin probe were in this case approximately 0.5 V more positive than those obtained with the CSE. A calibration is thus possible for comparisons with conventional test results, keeping in mind that the conversion can vary with disk surface condition.

Figure 7:
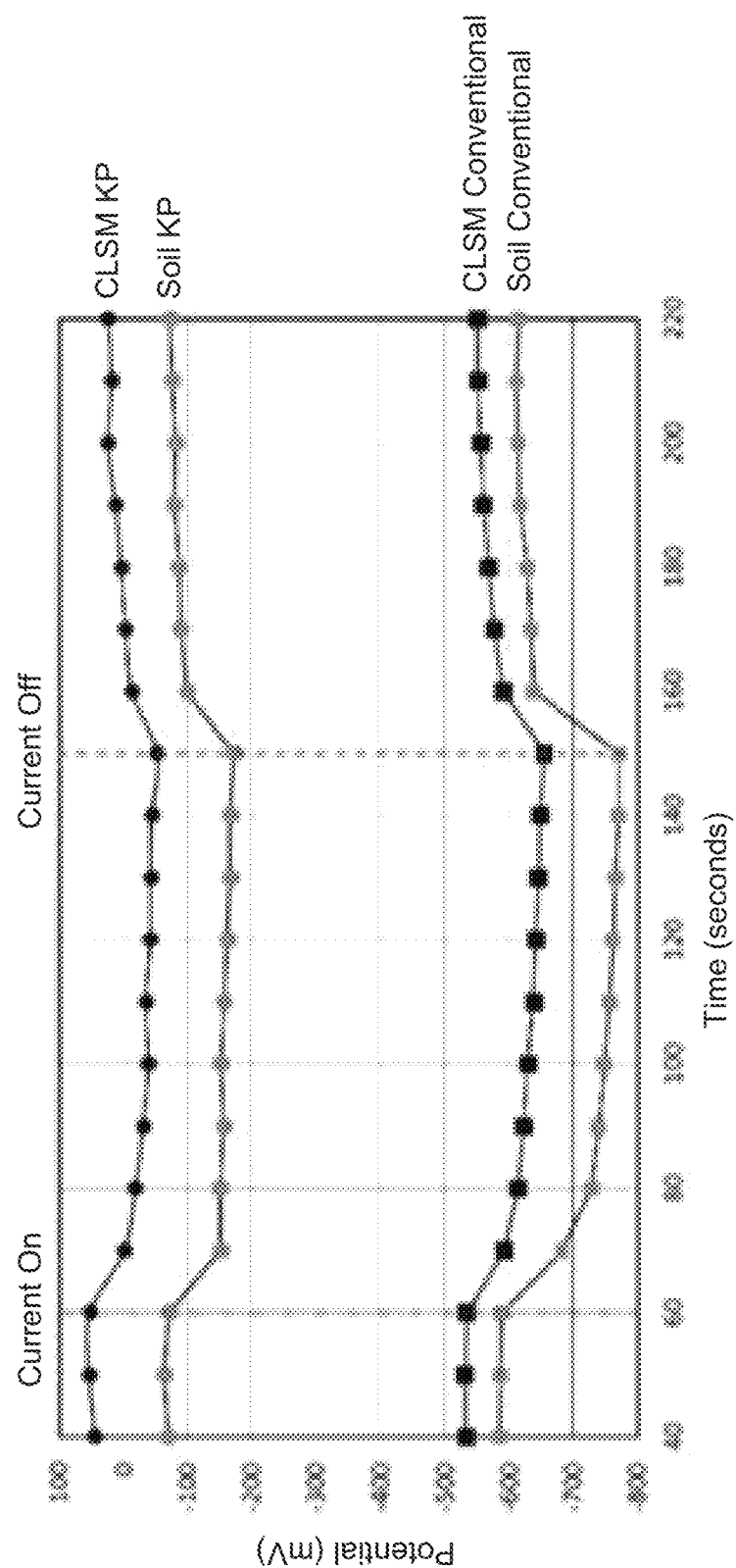
FIG. 7 is a graph that plots the impressed current response of reinforcement showing successful Kelvin probe replication of trends obtained through conventional CSE.

As the native corrosion macrocell was weak, a stronger impressed current test was conducted, which served to assess the ability of the probe to detect the presence of combined interfacial and ohmic potentials. When a controlled current of approximately 1.2 mA was applied to the surface anode, the Kelvin probe successfully measured a discernable response (~100 mV potential shift, plus dynamic response as a function of time) directly above the cathodically protected galvanized reinforcement. This response was verified with a CSE electrode in place of the Kelvin probe, where a response of approximately equal magnitude (offset as indicated earlier) was observed during polarization and depolarization cycles, as shown in FIG. 7.

Figures 8A, 8B:
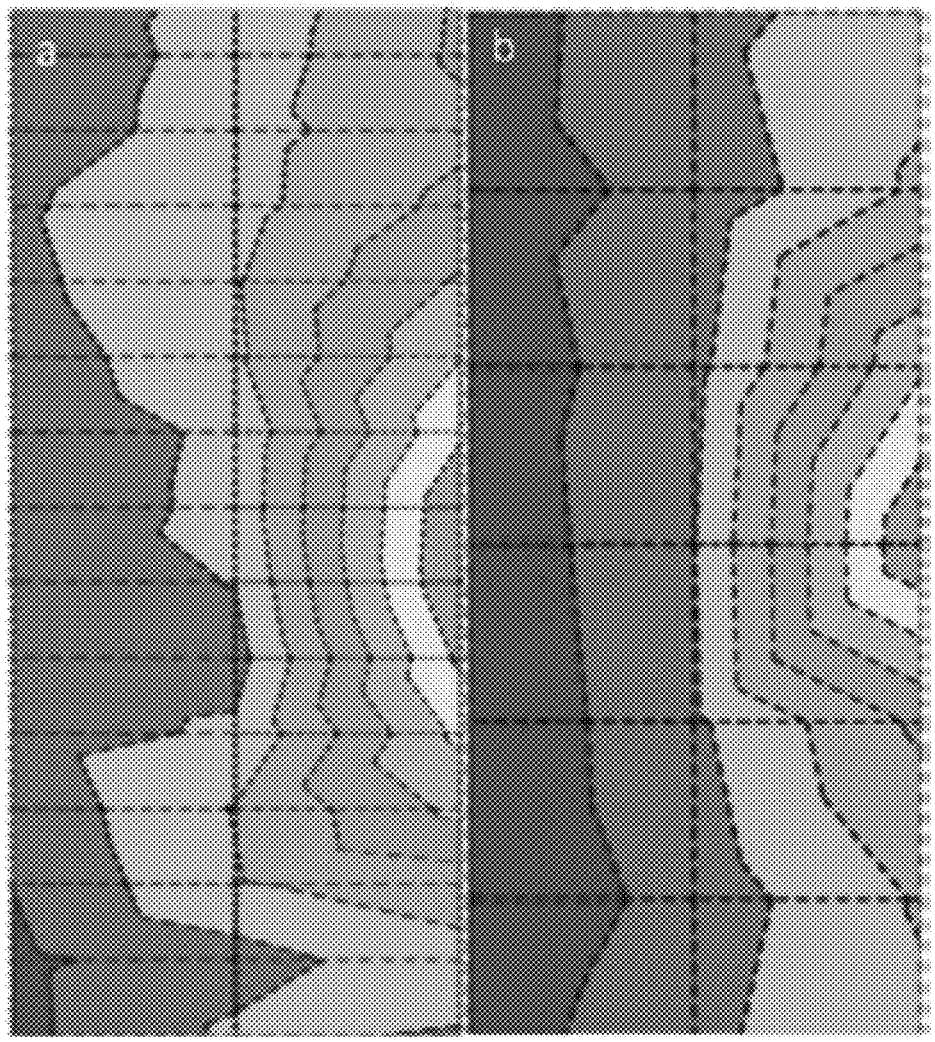
FIGS. 8A and 8B are potential maps obtained during a polarization regime using a dual Kelvin probe array (8A) and conventional CSE (8B). The potential maps show most the anodic location near the anode on right side of box.

The dual-sensor array enabled scanning of the surface potential in consecutive parallel tracks for rapid acquisition of a potential map. FIG. 8 exemplifies results for the central, approximately 1.8×0.6 m, portion of the surface. The translation speed was approximately 15 cm/sec with data deconvoluted to account for sensor response time. The map obtained with the dual-sensor array (FIG. 8A) successfully reproduced the main features and anode location signature obtained with the traditional, but slower, CSE survey (FIG. 8B).

From this testing, it was observed that a contactless macroscopic scanning Kelvin probe can be successfully used to measure potential on the surfaces of CLSM- and soil-embedded galvanized steel reinforcements. The response was also suitable for calibration against a conventional CSE. The Kelvin probe potential measurements were rapid, stable, and reproducible enough for constructing surface maps that can be used in corrosion assessments, without any disturbance of the CLSM or soil surface. The Kelvin probe successfully operated under dynamic conditions representative of a cathodic protection installation, showing capability for electrochemical diagnostic operations. The dual-sensor array was successfully capable of mapping out simulated cathodic protection conditions.

These results are significant as Kelvin probes have never before been used to evaluate reinforcement members when buried in soil. Although Kelvin probe testing has been used in other applications, soil presents a unique challenge as it does not have a well-defined surface like man-made materials, such as a piece of metal. Unlike such man-made materials, the surface of soil comprises organic particulate matter that makes for a rough, inconsistent surface. In such a case, it is difficult to say where the "surface" actually lies. For instance, is the "surface" the location of the highest pieces of particulate matter, which may include loose particles, or is it somewhere deeper in the soil at a point at which a particular constant density is achieved? Moreover, as the Kelvin probe comprises a linearly vibrating disk that moves toward and away from the test surface, it was not clear whether or not this would disturb the soil surface and somehow skew the results. As the above-described test results establish, however, unexpectedly reliable results can be achieved using a Kelvin probe on soil in spite of these complicating factors.

The invention claimed is:

1. A method for non-contact assessment of reinforced soil, the method comprising:
    positioning a reference electrode in close proximity to a surface of the soil without contacting the electrode to the soil surface;
    providing a surface anode on the soil surface to simulate a cathodic protection system;
    vibrating the electrode with a vibration generator; and
    measuring an electrical potential difference between the electrode and the soil surface, the potential difference being indicative of the condition of a portion of a reinforcement member positioned below the soil surface at the location of the electrode.

2. The method of claim 1, wherein suspending the electrode comprises suspending the electrode with a stem that extends downward from the vibration generator.

3. The method of claim 1, wherein vibrating the electrode comprises vibrating the electrode with an electromagnetic voice coil that linearly displaces the electrode in response to a magnetic field generated from current passing through the coil.

4. The method of claim 1, wherein measuring the electrical potential difference comprises applying a voltage to the reinforcement member and obtaining a signal from the reference electrode in an absolute measurement scheme.

5. The method of claim 1, wherein measuring the electrical potential difference comprises applying a voltage to the surface of the soil at a location near the location of the reference electrode and obtaining a signal from the reference electrode in a differential measurement scheme.

6. The method of claim 1, wherein measuring the electrical potential difference comprises applying a voltage to the surface of the soil at a location near the reference electrode with a counter electrode and obtaining a signal from the reference electrode in a dynamic measurement scheme.

7. The method of claim 1, wherein measuring the electrical potential difference comprises amplifying a signal obtained from the reference electrode.

8. The method of claim 1, wherein measuring the electrical potential difference comprises obtaining a signal from the reference electrode and converting it into an electrical potential.

9. The method of claim 1, further comprising distributing the weight of a system that comprises the reference electrode across the soil surface using a force distribution member.

10. The method of claim 1, further comprising measuring the surface topography of the soil surface and using the topography measurements to increase the accuracy of the measurement of the electrical potential difference.

11. A non-contact reinforced soil assessment system, the system comprising:
    a measurement unit including a reference electrode adapted to be positioned in close proximity to a surface of reinforced soil to be assessed, a vibration generator connected to the reference electrode and adapted to vibrate the electrode, and a surface anode that can be used to simulate a cathodic protection system; and
    a control unit adapted to control activation of the vibration generator and obtain measurement signals from the reference electrode indicative of an electrical potential difference between the electrode and the soil surface.

12. The system of claim 11, wherein the reference electrode comprises a metal disk having a planar surface that faces the soil surface.

13. The system of claim 12, wherein the vibration generator comprises an electromagnetic voice coil that linearly displaces the electrode in response to a magnetic field generated from current passing through the coil, and wherein the metal disk is supported by an elongated stem that extends from the vibration generator.

14. The system of claim 11, wherein the measurement unit comprises adjustable feet that support the measurement unit on the solid surface and maintains desired spacing between the reference electrode and the soil surface.

15. The system of claim 11, wherein the measurement unit comprises wheels that enable the measurement unit to be pulled across the soil surface to take multiple measurements along a length of the surface.

16. The system of claim 15, further comprising a force distribution member that can distribute the force applied by the wheels to the soil surface.

17. The system of claim 11, wherein the measurement unit includes multiple reference electrodes aligned in an array across a width of the unit.

18. The system of claim 11, further comprising means for measuring the topography of the soil surface.

* * * * *